United States Patent
Buettner et al.

(10) Patent No.: US 7,851,661 B2
(45) Date of Patent: Dec. 14, 2010

(54) METHOD FOR PRODUCING DINITROTOLUENE

(75) Inventors: Johannes Buettner, Ruhland (DE); Wolfgang Mackenroth, Bad Duerkheim (DE); Heinrich Hermann, Cologne (DE); Peter Konieczny, Teltow (DE); Juergen Gebauer, Troisdorf (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 962 days.

(21) Appl. No.: 10/586,683

(22) PCT Filed: Feb. 2, 2005

(86) PCT No.: PCT/EP2005/001017
§ 371 (c)(1),
(2), (4) Date: Jul. 20, 2006

(87) PCT Pub. No.: WO2005/075407
PCT Pub. Date: Aug. 18, 2005

(65) Prior Publication Data
US 2008/0242900 A1     Oct. 2, 2008

(30) Foreign Application Priority Data
Feb. 5, 2004     (DE)     ........... 10 2004 005 913

(51) Int. Cl.
*C07C 205/00*     (2006.01)
(52) U.S. Cl. .................. 568/934; 568/939; 568/927
(58) Field of Classification Search .............. None
See application file for complete search history.

(56) References Cited

U.S. PATENT DOCUMENTS

| | | | |
|---|---|---|---|
| 2,362,743 | A | 11/1944 | Crater |
| 2,947,791 | A | 8/1960 | Adams et al. |

(Continued)

FOREIGN PATENT DOCUMENTS

EP     0 066 202     12/1982

(Continued)

OTHER PUBLICATIONS

Hermann et al., "Industrial Nitration of Toluene to Dinitrotoluene", ASC-Symphosium, series 623, pp. 234-249, 1996.

*Primary Examiner*—Daniel M Sullivan
*Assistant Examiner*—Clinton Brooks
(74) *Attorney, Agent, or Firm*—Oblon, Spivak, McClelland, Maier & Neustadt, L.L.P.

(57) ABSTRACT

The present invention provides a process for preparing dinitrotoluene, comprising the steps of
  a) reacting toluene with nitric acid in the presence of sulphuric acid to give mononitrotoluene,
  b) separating the reaction product from step a) into an organic phase comprising mononitrotoluene and an aqueous phase comprising sulfuric acid,
  c) reacting the organic phase comprising mononitrotoluene with nitric acid in the presence of sulphuric acid to give dinitrotoluene,
  d) separating the reaction product from step c) into an organic phase comprising dinitrotoluene and an aqueous phase comprising sulfuric acid,
wherein the reaction product from step a) has a content of toluene of from 3.0 to 8% by weight, based on the organic phase, and a content of nitric acid of from 0.1 to 1.2% by weight, based on the aqueous phase, and the phase separation in step b) is effected in such a way that further reaction of the toluene with the nitric acid is prevented.

14 Claims, 2 Drawing Sheets

U.S. PATENT DOCUMENTS

| | | |
|---|---|---|
| 3,092,671 A | 6/1963 | Humphrey et al. |
| 3,434,802 A | 3/1969 | Toischer et al. |
| 4,367,347 A | 1/1983 | Sawicki |
| 4,663,490 A | 5/1987 | Gerken et al. |
| 5,275,701 A | 1/1994 | Mazzafro et al. |
| 5,679,873 A | 10/1997 | Klingler et al. |
| 5,689,018 A * | 11/1997 | Klingler et al. ............ 568/934 |
| 5,948,944 A | 9/1999 | Zhang et al. |
| 2002/0091290 A1 | 7/2002 | Demuth et al. |

FOREIGN PATENT DOCUMENTS

| | | |
|---|---|---|
| EP | 0 155 586 | 9/1985 |
| EP | 0 597 361 | 5/1994 |
| EP | 0 696 570 | 2/1996 |
| EP | 0 696 571 | 2/1996 |
| EP | 0 736 514 | 10/1996 |
| EP | 0 903 336 | 3/1999 |
| PL | 126089 | 7/1983 |

\* cited by examiner

METHOD FOR PRODUCING DINITROTOLUENE

The invention relates to a process for preparing dinitrotoluene (DNT) by nitrating toluene with nitric acid in the presence of sulfuric acid in two stages in countercurrent.

Dinitrotoluene (DNT) is an intermediate for the preparation of toluene diisocyanate (TDI), together with methylene diisocyanate (MDI) the most important precursor for the preparation of polyurethanes.

The nitration of toluene to DNT is effected, as described, for example, in H. Hermann, J. Gebauer, P. Konieczny, Industrial Nitration of Toluene to Dinitrotoluene in ASC Symposium, series 623, 234-249, 1996 ed. L. F. Albright, R. V. C. Carr, R. J. Schmitt, predominantly isothermally using nitric acid in the presence of sulfuric acid (mixed acid) as the catalyst in two stages continuously in countercurrent in a two-phase system, in such a way that, at the stage of the nitration of toluene to mononitrotoluene (MNT) (MNT stage), the waste acid obtained from the DNT stage is concentrated with the nitric acid and mixed with the toluene, the phases are separated after conversion of the toluene to MNT and the MNT is reacted in a second stage (DNT stage) with nitric acid in the presence of sulfuric acid to give DNT.

The waste acid from the nitration of the first stage, having a sulfuric acid content of at least from 70 to 71%, a residual content of nitric acid of from 0.1 to 0.5%, a content of nitrose of from 0.4 to 1.5% by weight, reported as nitrous acid ($HNO_2$), still-dissolved MNT of from approx. 0.2 to 0.45% and a maximum water content of from 26.6 to 29.3%, is fed to a purification before reuse, such as recycling into the nitration process after concentration.

The crude MNT which, in addition to traces of toluene in the range from 0.1 to 0.3% by weight, still comprises nitric acid, nitrogen dioxide ($NO_2$), nitrocresols and the DNT still dissolved in the waste acid from the nitration of the second stage is introduced into the DNT stage and reacted there fully with a fresh mixture of nitric acid and sulfuric acid to give DNT in such a way that DNT according to the desired specification, such as MNT content <0.1%, TNT content <500 ppm, ortho isomers max. 4.5%, is obtained. After separation of the phases, the crude DNT is washed in such a way that the nitric and sulfuric acid dissolved in the DNT can for the most part be recovered and fed into the nitration at the MNT stage (see EP 0 736 514).

The waste acid from the DNT stage, having a sulfuric acid concentration of from approx. 78.0 to 79.0 percent, nitric acid of from approx. 1 to 1.5% and nitrose from the oxidation of the nitrocresols in the MNT of approx. 0.8-1.5%, is, after concentration with fresh nitric acid, used in the MNT stage as mixed acid for nitration.

The sulfuric acid used for the nitration of MNT to DNT is typically sulfuric acid having a content of about 96% which is either freshly prepared or obtained by concentrating the waste acid from the MNT stage in a reconcentration plant.

Aside from this standard process of 2-stage continuous isothermal nitration, EP 903 336 also proposes carrying out the nitration of toluene to DNT continuously with mixed acid in 3 stages or adiabatically in one or two stages in such a way that, as described in EP 597 361 and EP 696 570, the entire heat of reaction from the nitration of toluene to DNT, or only from the DNT stage as described in EP 696 571, is utilized to remove the water of reaction from the nitration and the water introduced into the waste acid by the nitric acid. In addition, U.S. Pat. No. 5,948,944 and U.S. Pat. No. 2,362,743 propose carrying out the nitration of toluene to DNT only in nitric acid as the reaction medium and thus avoiding the use of sulfuric acid.

In all processes for preparing DNT by nitrating toluene, it is a prerequisite for economic process control that the reaction medium, for example sulfuric acid or nitric acid, is worked up again in such a way that it can be reused as the reaction medium in the nitration process, as described, for example, in EP 155 586 and U.S. Pat. No. 5,275,701.

It is crucial for the selection of a nitration process, also for reasons of environmental pollution, that the losses of acids, both sulfuric and nitric acid, as a result of side reactions are as small as possible.

One way in which this aim is typically achieved is that the water is removed from the waste sulfuric acid from the nitration to MNT after a removal of the still-dissolved nitroaromatics whose content, depending on the MNT/DNT ratio in the waste acid and the concentration of sulfuric acid in the waste acid, is from 0.15 to 0.45%, from the nitric acid and from the nitrose in a single- to multistage process down to a sulfuric acid concentration which allows this concentrated sulfuric acid to be recycled into the DNT nitration stage as fresh acid having a concentration of from 88 to 94% sulfuric acid or after a further concentration in a superconcentration stage to from 94 to 98% sulfuric acid, as described, for example, in EP 155 586.

To minimize the losses of nitric acid which are not converted to the end product, as described, for example, in EP 0 736 514, the nitric acid from the scrubbing of the crude DNT, as a weak acid having a total acid content of from 23.73 to 40% total acid, together with the nitric add from the offgas scrubbing and the stripping of the waste acid, is recycled into the nitration directly or after concentration. In addition to the improvement in the yield of DNT based on the nitric acid used to up to above 98%, this simultaneously substantially reduces the nitrate pollution of the wastewater.

When semiconcentrated sulfuric acid from the nitration of toluene to MNT is used for the preparation of DNT, there is no need to fully remove all impurities from the nitration from the semiconcentrated sulfuric acid before recycling into the nitration.

This makes it possible to work even with small degrees of workup, for example from 88 to 94% sulfuric acid which still comprises traces of DNT and nitrose, without the product quality being adversely affected. This allows the costs of sulfuric acid concentration to be kept low, since the costly and inconvenient superconcentration of sulfuric acid may be dispensed with.

In addition to closed circulation of sulfuric acid in the process with minimum consumption of sulfuric acid and a conversion of the nitric acid used of more than 98% to the product, further costly and inconvenient technical measures are additionally needed for a modern plant to continuously prepare DNT isothermally from toluene in two stages in countercurrent, in order to be able to carry out "controlled nitration".

It is thus necessary to prevent undefined operating states during the nitration and thus to prevent the occurrence of "uncontrolled" nitration, associated with high evolution of heat, which can lead to explosion in an extreme case. This catalog of requirements applies in particular when the highly reactive toluene is still present in the reaction mixture.

This is typically achieved by
a) working in countercurrent in two defined stages in such a way that only toluene is converted to MNT in the MNT stage using a nitrating acid and under conditions under which uncontrolled further conversion of the MNT formed to DNT is substantially ruled out at the given residence time, and the MNT is fully converted to DNT at the DNT stage in accordance with the specification, b) in all nitration stages, nitrating only in the waste acid at very low sulfuric acid and nitric acid concentration, c) the biphasic nitration mixture always being present in the reactor as a homogeneous emulsion, d) the heat of reaction from the nitration and from the admixing of concentrated mixed acids to the reaction mixture being removed effectively, which is only possible when, as well as sufficient cooling surface on addition of product to be nitrated, such as toluene and MNT, the nitration mixture is present as an emulsion, e) the proportion of unconverted product (toluene, MNT) in the reaction mixture being as low as possible in the individual reactors, f) the phases of the nitration mixture only being separated into organic and acid phase in the presence of excess nitric acid when only small amounts, if any, of product to be nitrated are present in the organic phase, g) the phases of the nitration mixture having product which is yet to be fully converted (toluene, MNT) being separated only when the nitric acid content in the nitration acid is 0 or so low that the heat of reaction released in an uncontrolled nitration cannot lead to undefined states of operation such as decomposition, outgassing, etc.

This catalog of requirements applies in particular when unconverted toluene is still present in the reaction mixture.

A controlled nitration fulfills these safety requirements when a phase separation of the nitration mixture is carried out only when no product to be nitrated is present any longer in the organic phase in question at the particular nitration stage (toluene in the MNT stage and MNT in the DNT stage) and the nitric acid content is as low as possible.

In the existing industrial processes, the phase separation is typically effected at the MNT stage when more then 99.5% of the toluene has been converted, described, for example, in EP 903 336, U.S. Pat. No. 3,092,671 and EP 066 202, corresponding to a toluene content of from approx. 0.1 to 0.5%, see, for example, H. Hermann, J. Gebauer, P. Konieczny, Industrial Nitration of Toluene to Dinitrotoluene in ASC Symposium, series 623, 234-249, 1996 ed. L. F. Albright, R. V. C. Carr, R. J. Schmitt, Tab. II.

In that case, the nitric acid content in the MNT waste acid is typically from approx. 0.4 to 1.0% nitric acid. Under these conditions, uncontrolled nitration in the organic phase is no longer possible for the lack of toluene. The entire heat of reaction which arises from the conversion of the toluene to MNT was removed in a defined manner under the conditions of a controlled nitration.

Conversely, when a noticeable content of toluene is still present in the MNT at the MNT stage, for example of from 3.5 to 5% in the MNT, the phase separation is not carried out until there is no longer any nitric acid in the waste acid at the time of phase separation, but rather it has been fully consumed before the phase separation; see U.S. Pat. No. 2,947,791.

In addition to these continuous industrial processes with defined conditions per process stage, PL 126 069 proposes preparing an MNT/DNT mixture as early as at the MNT stage and only then carrying out the phase separation in order to fully convert the remaining MNT in the MNT/DNT mixture in the DNT stage.

Under these conditions with the substantially less reactive MNT in a mixture with DNT and in the presence of a waste acid having a sulfuric acid concentration which only allows a slow conversion of MNT to DNT, the risk of uncontrolled reactions is substantially reduced.

To attain a substantially complete selective conversion of the toluene at the MNT stage, the sulfuric acid concentration in the nitrating acid and the reaction temperature in the existing industrial processes are selected in such a way that only MNT is formed but a further reaction to give DNT occurs very slowly if at all.

This two-stage procedure with selective conversion of the toluene to MNT at a reaction temperature of preferably from 35 to 45° C., a waste acid having preferably from 70 to 72% sulfuric acid and a nitric acid content of preferably from 0.3 to 0.7% in the MNT stage and, in the DNT stage, at a reaction temperature of preferably from 60 to 70° C., a waste acid with preferably from 80 to 82% sulfuric acid (without the dissolved DNT in the DNT waste acid) and a nitric acid content of preferably from 1.0 to 1.5% in the DNT stage offers the advantage that the reaction partners, toluene and nitric acid, at the MNT stage, or nitric acid and sulfuric acid, at the DNT stage, can be added stoichiometrically by simple metering under mass control, and there is no need for any costly and inconvenient analytical checking of the reaction mixture during the nitration at the individual stages, as is necessary when a mixed nitration to give MNT/DNT mixtures is effected in the MNT stage with sulfuric acid concentrations in the MNT waste acid with which a noticeable conversion of the MNT to DNT is already possible in the presence of unconverted toluene.

For this selective full conversion of toluene in the MNT stage or of MNT in the DNT stage in the continuous isothermal nitration of toluene to DNT in two stages in countercurrent, it is customary to carry out the nitration in stirred tank batteries at the individual stages. For instance, U.S. Pat. No. 3,434,802, EP 903 336, EP 066 202, PL 126 089 and U.S. Pat. No. 2,947,791 propose carrying out the industrial nitration of toluene to MNT in a two- to four-stage stirred tank battery, and likewise carrying out the conversion of MNT to DNT in a two- to four-stage stirred tank battery.

In this procedure, in conjunction with the appropriate nitrating acids, not only is a conversion of the toluene in the MNT stage of more than 99.5% attained, but also DNT which complies with the required specifications for purity (MNT<0.1%, TNT<0.1%) at industrially practicable residence times of the nitration mixture in the individual continuous cocurrent nitration stages conducted in countercurrent.

Figure 1:
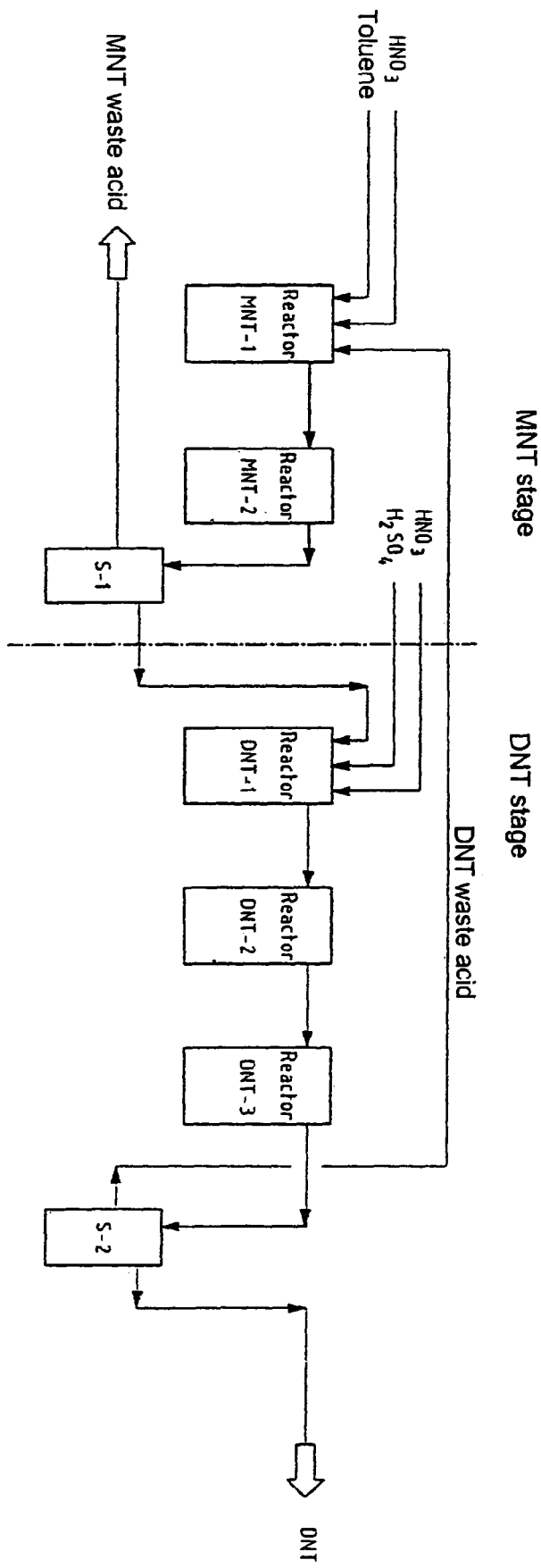
FIG. 1 shows the process flow diagram for the Comparative Example 1.

It is an object of the invention to further simplify the process for preparing DNT, especially in relation to the number of apparatus used in conjunction with a reduction in the reaction volume and in particular to reduce the number of reactors used.

It has now been found that, surprisingly, it is possible to carry out the isothermal nitration of toluene to DNT, in a departure from the prior art nitration conditions, in such a way that, at the MNT stage at the time of phase separation, there is still an elevated toluene content in the MNT and simultaneously also still a nitric acid content in the nitrating acid without the occurrence of undefined operating states with corresponding safety risks, as long as the phase separation of MNT from the waste acid is effected in such a way that further reaction of the toluene with the nitric acid is reliably prevented.

The invention thus provides a process for preparing dinitrotoluene, comprising the steps of
a) reacting toluene with nitric acid in the presence of sulfuric acid to give mononitrotoluene,
b) separating the reaction product from step a) into an organic phase comprising mononitrotoluene and an aqueous phase comprising sulfuric acid,
c) reacting the organic phase comprising mononitrotoluene with nitric acid in the presence of sulfuric acid to give dinitrotoluene,
d) separating the reaction product from step c) into an organic phase comprising dinitrotoluene and an aqueous phase comprising sulfuric acid, wherein the reaction product from step a) has a content of toluene of 0.1-10% by weight, preferably from 0.5 to 8% by weight, in particular from 3.5 to 5% by weight, based on the organic phase, and a content of nitric acid of from 0.1 to 1.2% by weight, based on the aqueous phase, and the phase separation in step b) is effected in such a way that further reaction of the toluene with the nitric acid is prevented.

The further reaction may in particular be prevented by a rapid and effective separation of the organic and the inorganic phase. Such a separation is possible, for example, by means of dynamic separators.

The organic phase from step b) may be transferred to step c) without further workup.

The aqueous phases from steps b) and d), if appropriate after workup and concentration, may be reused in step a) and step c). The concentration is typically effected by removing the water, especially by means of distillation. After the concentration, the sulfuric acid preferably has a concentration in the range between 85 and 96%.

The temperature of stage a) is preferably in the range between 35 and 70° C., preferably between 45 and 55° C.

The molar ratio of nitric acid to toluene in step a) is preferably in the range between 0.95 and 1.12. The molar ratio of nitric acid to MNT in step c) is preferably between 1.03 and 1.10.

The temperature in stage c) is usually in the range between 60 and 85° C., preferably in the range between 65 and 80° C.

The concentration of the nitric acid used in stages a) and c) is typically between 58 and 100%. In practice, it is customary to work either with a nitric acid concentration in the range between 58 and 68% or with a nitric acid concentration in the range between 95 and 99.9%.

MNT having the inventive residual contents of toluene and nitric acid at the time of phase separation may be obtained with the customary number of from 2 to 4 stirred tanks under otherwise identical nitration conditions when operation is effected at low nitration temperatures, as described in U.S. Pat. No. 3,708,546, or the nitration is carried out at a sulfuric acid concentration of from 62 to 64% in the waste acid. Neither procedure is very suitable for industrial scale preparation of DNT.

A further possibility for achieving the inventive contents of toluene and nitric acid is, contrary to the customary procedure, not to carry out the nitration of toluene to MNT in a multistage stirred tank battery, but rather only in one stirred tank, and then to carry out the phase separation. Under otherwise identical reaction conditions to the multistage stirred tank battery, the shortening of the residence time by approx. 50% results in the toluene not being fully converted.

Variation of the nitration temperature in stage a), for example a temperature increase in the reactor to 55° C., allows the toluene content in the MNT and the nitric acid content in the nitrating acid to be adjusted precisely.

In the prior art, it was customary in the two-stage nitration of toluene to DNT in countercurrent by the standard process to use at least two reactors at the MNT stage, in which case, for example, the toluene, nitric acid and the DNT end acid are either only fed into one reactor of stage a) and the other reactor served as a delay vessel, or the nitric acid is fed together with a portion of the toluene into a reactor of stage a) and the remainder of the toluene into the second reactor of stage a) in order to optimize the 2,4-, 2,6-DNT isomer ratio.

It has now been found that, surprisingly, it is possible to convert from approx. 85 to 95% of the toluene used in the first reactor of the MNT stage. Such MNT is in equilibrium with a nitrating acid of from approx. 72 to 73% sulfuric acid and a nitric acid content of max. 1.2% at a nitration temperature of 55° C.

When operation is effected in stage a) only with one reactor and the phase separation of the nitration mixture is carried out directly downstream of the reactor in such a way that there can be no uncontrolled further reaction, and the thus obtained MNT is fed directly into the DNT stage with up to 10% toluene, it is found that, surprisingly, in comparison to the standard process in which operation is effected with MNT having a toluene content of <0.2% after the phase separation, it is also possible to convert MNT having a residual toluene content of up to 10% to DNT which satisfies all specification parameters. The formation of by-products such as nitrocresols and nitrose is also unchanged.

Surprisingly, there is no need to adjust the metering of nitric acid at the MNT stage and of sulfuric acid and nitric acid at the DNT stage in accordance with the changed conversions at the individual stages.

This unexpected behavior demonstrates the high buffer capacity of the nitration mixtures against slight variations in metering of toluene, nitric acid and sulfuric acid. The incomplete conversion of the toluene of up to 15% of the amount used at the MNT stage makes it unnecessary to change the metering ratios which are optimal from a safety point of view for the individual stages.

It has additionally been found that, instead of a three- to four-stage reactor, especially stirred tank battery, for the DNT stage, it is also possible without any problem to fully convert MNT having a toluene content of up to 10% in a reactor, especially stirred tank battery, consisting of a maximum of two reactors with reduced residence time. Here too, variation of the nitration temperature, for example an increase in the temperature in the first and second or else only in the second reactor to up to 85° C., additionally allows the residual MNT content in the DNT to be adjusted to <0.1%. An additional advantage of working with only two reactors at the DNT stage is that the content of trinitrotoluene (TNT) in the DNT decreases significantly and can even fall below the detection limit.

The slightly increased residual content of nitric acid in comparison to a full conversion of the toluene in two reactors of approx. 1.2% in the waste acid from the MNT stage is likewise recovered in the course of the reprocessing of the waste nitric acid for the purpose of recycling into the nitration, and recycled into the nitration.

The invention is to be illustrated in detail using the examples which follow.

General nitration conditions for Example 1 (Comparative example, FIG. 1) and Example 2 (Inventive example, FIG. 2):

In Example 1, operation was effected in the MNT stage using two stirred tanks and in the DNT stage using three stirred tanks. In Example 2, operation was effected in the MNT stage using one stirred tank and in the DNT stage using two stirred tanks.

870 kg of 94.5% sulfuric acid from the reprocessing of MNT waste acid were fed together with 372 kg of 99.7% nitric acid and the MNT from the MNT stage, after phase separation in the separator S1, into the reactor DNT-1 of the DNT stage.

After the reaction mixture had passed through the stirred tank battery of the DNT stage (DNT-1 to DNT-n), the DNT/DNT waste acid mixture was separated in the separator S2.

The DNT (1000 kg) was freed in a downstream scrubbing of all acidic impurities (nitric acid, sulfuric acid, nitrose) and the nitrocresols.

The waste acid was fed into the MNT stage in reactor MNT-1 with 519 kg of toluene and 341 kg of 99.7% nitric acid together with the recovered nitric acid from the scrubbing of the DNT and the reprocessing of the MNT waste acid.

After the reaction mixture had passed through the stirred tank battery of the MNT stage (MNT-1 to MNT-n), the MNT/MNT waste acid mixture was separated in the separator S1. The crude MNT was fed into the DNT stage as described above.

The MNT waste acid was freed of the dissolved nitroaromatics, the residual nitric acid and the nitrose and recycled into the process after concentration to 94.5% sulfuric acid.

Figure 2:
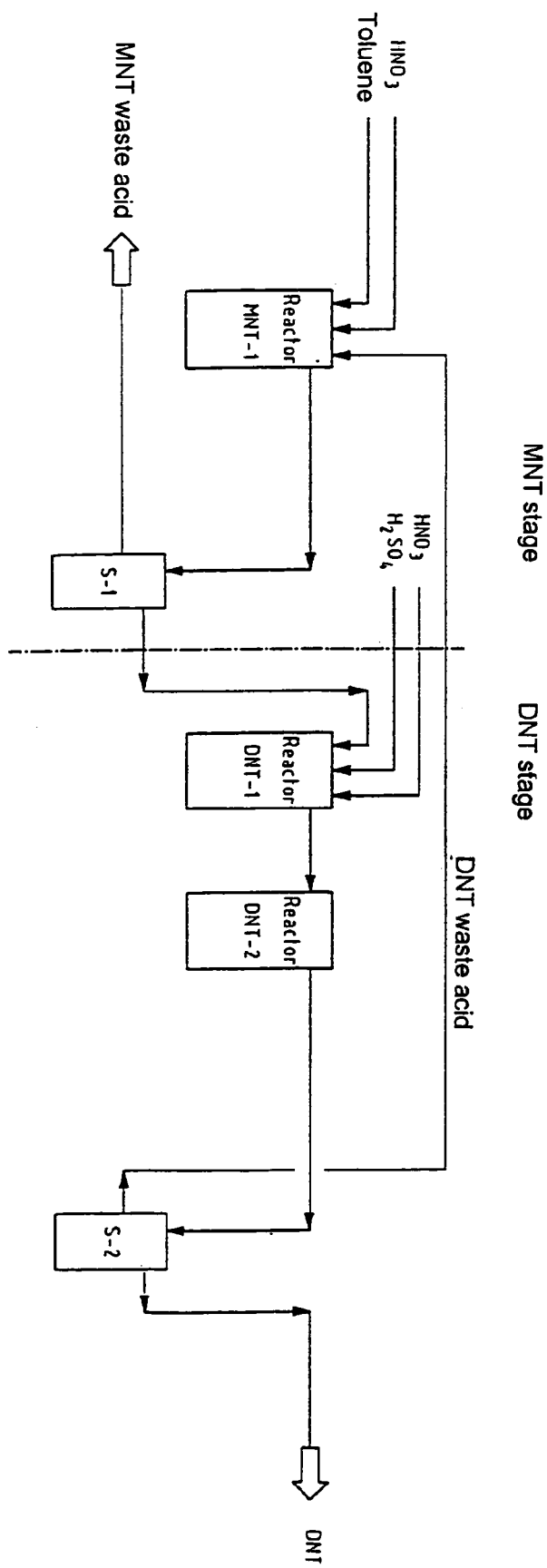
FIG. 2 shows the process flow diagram for Example 2 as an embodiment of the invention.

Table 1 compiles the compositions of the waste acid and of the products for nitration by the standard process (2 reactors at the MNT stage, 3 reactors at the DNT stage, FIG. 1) and for the process according to the invention (1 reactor in the MNT stage, 2 reactors in the DNT stage, FIG. 2).

The comparison of the nitration and product parameters for a nitration of toluene to DNT by the standard process having a total of 5 reactors with the improved process having only 3 reactors shows that without changing the metering parameters for toluene, nitric acid and sulfuric acid in the individual nitration stages, it is possible to prepare MNT having up to 5% toluene in the MNT stage and to convert it without any problem to on-spec DNT in the DNT stage, without the optimal nitration conditions developed for an industrial nitration having to be changed in comparison to the standard process.

The waste acids from the MNT and the DNT stage as an indicator of problem-free progress of the nitration, in the improved process with a reduced number of reactors, have the same composition as in the standard process.

The invention claimed is:

1. A process for preparing dinitrotoluene, comprising:
    a) reacting toluene with nitric acid in the presence of sulfuric acid to give a mononitrotoluene reaction mixture;
    b) separating the mononitrotoluene reaction mixture from a) in a dynamic separator into an organic phase comprising mononitrotoluene and an aqueous phase comprising sulfuric acid;
    c) reacting the organic phase comprising mononitrotoluene with nitric acid in the presence of sulfuric acid to give a dinitrotoluene reaction mixture; and
    d) separating the dinitrotoluene reaction mixture from c) into an organic phase comprising dinitrotoluene and an aqueous phase comprising sulfuric acid;
    wherein the mononitrotoluene reaction mixture from a) has a content of toluene of 3.5 to 8% by weight, based on the organic phase, and a content of nitric acid of from 0.1 to 1.2% by weight, based on the aqueous phase, and the phase separation in b) is effected in such a way that further reaction of the toluene with the nitric acid is prevented.

2. The process according to claim 1, wherein the content of toluene in the organic phase of the mononitrotoluene reaction mixture is from 3.5 to 5% by weight.

3. The process according to claim 1, wherein the organic phase comprising mononitrotoluene from b) is transferred to c) without further workup.

4. The process according to claim 1, wherein the aqueous phases comprising sulfuric acid from b) and d) are reused in a) and c).

5. The process according to claim 1, wherein the reaction of toluene with nitric acid in a) and the reaction of the organic phase comprising mononitrotoluene c) are conducted in apparatus selected from the group consisting of stirred tanks, flow reactors and both stirred tanks and flow reactors.

6. The process according to claim 1, wherein a) is carried out in one reaction apparatus.

7. The process according to claim 1, wherein c) is carried out in a maximum of two reaction apparatus connected in series.

8. The process according to claim 1, wherein a temperature of the reaction of toluene with nitric acid in a) is in the range between 35 and 70° C.

9. The process according to claim 1, wherein a temperature of the reaction of the organic phase comprising mononitrotoluene c) is in the range between 60 and 85° C.

10. The process according to claim 1, wherein a molar ratio of nitric acid to toluene in the reaction of toluene with nitric acid in a) is in the range between 0.95 and 1.12.

11. The process according to claim 1, wherein a molar ratio of nitric acid to mononitrotoluene in the reaction of the organic phase comprising mononitrotoluene c) is in the range between 1.03 and 1.10.

TABLE 1

| MNT stage | Example 1 (Comparative) | Example 2 (Inventive) | DNT stage | Example 1 (Comparative) | Example 2 (Inventive) |
| --- | --- | --- | --- | --- | --- |
| Number of reactors | 2 | 1 | Number of reactors | 3 | 2 |
| Nitration temperature | 45° | 55° | Nitration temperature | 60-70° | 65-80° |
| MNT waste acid | | | DNT waste acid | | |
| Sulfuric acid % | 71.52 | 71.55 | Sulfuric acid % | 78.44 | 78.36 |
| Nitric acid % | 0.41 | 0.96 | Nitric acid % | 1.20 | 1.19 |
| Nitrous acid % | 1.19 | 1.28 | Nitrous acid % | 1.05 | 1.23 |
| Product (MNT) | | | Product (DNT) | | |
| Toluene % | <0.15 | 3.5 | MNT % | n.d. | n.d. |
| MNT % | 91.1 | 88.7 | TNT % | 0.01-0.02 | <0.01 |
| DNT % | 8.8 | 7.8 | 2,4-DNT % | 79.3 | 79.3 |
| | | | 2,6-DNT % | 20.7 | 20.7 |
| | | | Other isomers % | 4.79 | 4.82 |

12. The process according to claim 1, wherein the aqueous phase comprising sulfuric acid from b) is concentrated to give sulfuric acid having a concentration of from 85 to 96% and recycled in a).

13. The process according to claim 1, wherein the aqueous phase comprising sulfuric acid from d) is admixed with nitric acid and recycled into a).

14. The process according to claim 1, wherein the nitric acid supplied in a) and c) has a concentration of from 58 to 100% by weight $HNO_3$.

* * * * *